US011123495B2

(12) United States Patent
Scharf (10) Patent No.: US 11,123,495 B2
(45) Date of Patent: Sep. 21, 2021

(54) INJECTION DEVICE (71) Applicant: Sanofi-Aventis Deutschland GMBH, Frankfurt am Main (DE)

(72) Inventor: Peter Scharf, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 222 days.

(21) Appl. No.: 15/778,464

(22) PCT Filed: Nov. 21, 2016

(86) PCT No.: PCT/EP2016/078250
§ 371 (c)(1),
(2) Date: May 23, 2018

(87) PCT Pub. No.: WO2017/089261
PCT Pub. Date: Jun. 1, 2017

(65) Prior Publication Data
US 2018/0344946 A1 Dec. 6, 2018

(30) Foreign Application Priority Data

Nov. 27, 2015 (EP) .................... 15196678

(51) Int. Cl.
A61M 5/32 (2006.01)
A61M 5/20 (2006.01)
(52) U.S. Cl.
CPC ........ *A61M 5/3204* (2013.01); *A61M 5/2033* (2013.01); *A61M 5/3202* (2013.01);
(Continued)

(58) Field of Classification Search
CPC .............. A61M 5/3204; A61M 5/3202; A61M 5/3213; A61M 2005/3215
See application file for complete search history.

(56) References Cited

U.S. PATENT DOCUMENTS

2012/0232491 A1* 9/2012 Jennings ............. A61M 5/3204
604/192
2014/0114248 A1 4/2014 DeSalvo et al.
2014/0243753 A1 8/2014 Boström

FOREIGN PATENT DOCUMENTS

CA 1278729 1/1991
GB 2465389 5/2010
(Continued)

OTHER PUBLICATIONS

PCT International Preliminary Report on Patentability in International Appln. No. PCT/EP2016/078250, dated May 29, 2018, 7 pages.
(Continued)

*Primary Examiner* — Emily L Schmidt
(74) *Attorney, Agent, or Firm* — Fish & Richardson P.C.

(57) ABSTRACT

An injection device comprises an injector body arranged for mounting a syringe with a needle shield; and a cap disposed at one end of the injector body. The cap comprises a main body with a first open end and a second closed end, the main body comprising one or more openings through an outer surface; and an engaging member disposed externally on the main body, which comprises one or more protruding elements arranged to extend inwards through the one or more corresponding openings in the outer surface of the main body and configured to engage with the needle shield.

12 Claims, 4 Drawing Sheets (52) U.S. Cl.
CPC ............... *A61M 2005/206* (2013.01); *A61M 2005/2013* (2013.01)

(56) References Cited

FOREIGN PATENT DOCUMENTS

| JP | 2009-538661 | | 11/2009 | | |
|---|---|---|---|---|---|
| JP | 2014-530083 | | 11/2014 | | |
| WO | WO 2013/058697 | | 4/2013 | | |
| WO | WO 2014/154498 | | 10/2014 | | |
| WO | WO 2015/028488 | * | 3/2015 | .......... | A61M 5/3202 |
| WO | WO 2015/091850 | | 6/2015 | | |

OTHER PUBLICATIONS

PCT International Search Report and Written Opinion in International Appln. No. PCT/EP2016/078250, dated Feb. 20, 2017, 10 pages.

* cited by examiner

INJECTION DEVICE

CROSS REFERENCE TO RELATED APPLICATIONS

The present application is the national stage entry of International Patent Application No. PCT/EP2016/078250, filed on Nov. 21, 2016, and claims priority to Application No. EP 15196678.5, filed in on Nov. 27, 2015, the disclosures of which are incorporated herein by reference.

TECHNICAL FIELD

The present disclosure relates to an injection device and a cap for an injection device.

BACKGROUND

Injection devices, such as auto-injectors, are known in the art for dispensing a medicament to an injection site of a user. Such injection devices typically comprise a body and a cap. A needle syringe is located in the body. The cap is removably attached to the body to shield the needle of the needle syringe. To dispense the medicament, the cap is first removed from the body to expose the needle syringe.

The needle syringe is typically supplied with a needle shield in place, that is, a rubber sleeve which is fitted tightly over the needle to seal and protect the needle. The rubber needle shield must also be removed from the needle syringe to expose the needle for injection. The needle can then inserted into the body of the user at the injection site to dispense the medicament.

The cap of the injection device is typically large and easily removed. However, the rubber needle shield may be difficult to hold and therefore difficult to remove from the needle syringe. The proximity of the rubber needle shield to the needle makes some users uncomfortable about removing the needle shield.

SUMMARY

According to an aspect an injection device is provided, including an injector body arranged for mounting a syringe with a needle shield, and a cap disposed at one end of the injector body; the cap including a main body with a first open end and a second closed end, the main body including one or more openings through an outer surface; and an engaging member disposed externally on the main body, which comprises one or more protruding elements arranged to extend inwards through the one or more corresponding openings in the outer surface of the main body and configured to engage with the needle shield.

The one or more protruding elements may be formed as a plurality of barbs which are arranged to engage with the needle shield when the cap is pulled away from the injector body.

The one or more protruding elements may be formed as a plurality of hooks which are arranged to engage with the needle shield when the cap is pulled away from the injector body.

The engaging member may include a ring which is arranged externally around the main body. The one or more protruding elements may be arranged to extend inwards from the ring at an angle to a plane of the ring.

The main body may include a narrow portion, and the ring of the engaging member may be disposed around the narrow portion of the main body.

An open end of the main body may have an outer diameter which is larger than an outer diameter of the ring.

The open end of the main body may be configured to be compressed; and the open end of the main body may be arranged to pass through the ring of the engaging element when the open end of the main body is compressed.

The main body may include one or more slots extending from the open end thereof, the slots being configured to allow compression of the open end of the main body.

The main body may be a rubber material.

According to a further aspect a cap is provided for use with an injection device, wherein the cap includes a main body with a first open end and a second closed end, the main body including one or more openings through an outer surface, and an engaging member disposed externally on the main body, the engaging member including one or more protruding elements arranged to extend inwards through the one or more corresponding openings in the outer surface of the main body and configured to engage with a needle shield of the injection device.

The engaging member may include a ring which is arranged externally around the main body, and the one or more protruding elements may be arranged to extend inwards from the ring at an angle to a plane of the ring.

The one or more protruding elements may be formed as a plurality of barbs or a plurality of hooks.

An open end of the main body may be configured to be compressed; and the open end of the main body may be arranged to pass through the ring of the engaging element when the open end of the main body is compressed.

The main body may include one or more slots extending from the open end thereof, the slots being configured to allow compression of the open end of the main body.

According to a further aspect a method of manufacturing a cap for an injection device is provided, the method including forming a main body with a first open end and a second closed end, the main body including one or more openings through an outer surface; forming an engaging member, the engaging member including one or more protruding elements arranged to extend inwards through the one or more corresponding openings in the outer surface of the main body and configured to engage with a needle shield of the injection device; compressing the open end of the main body and passing the open end of the main body between the protruding elements of the engaging member; and passing the one or more protruding elements through the one or more openings of the main body.

These and other aspects of the invention will be apparent from and elucidated with reference to the embodiments described hereinafter.

BRIEF DESCRIPTION OF THE FIGURES

Exemplary embodiments of the present invention are described with reference to the accompanying drawings, in which.

DETAILED DESCRIPTION

Embodiments of the present disclosure provide an improved cap for an injection device or an auto-injector device. The cap includes an engaging element with a plurality of inwardly extending barbs for engaging with the rubber needle shield of a syringe within the injection device. The barbs attach to the rubber needle shield as the cap is pushed onto the injection device, and retain the rubber needle shield within the cap when it is removed from the device. The cap provides an improved injection device which does not require the rubber needle shield to be separately removed from the syringe.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
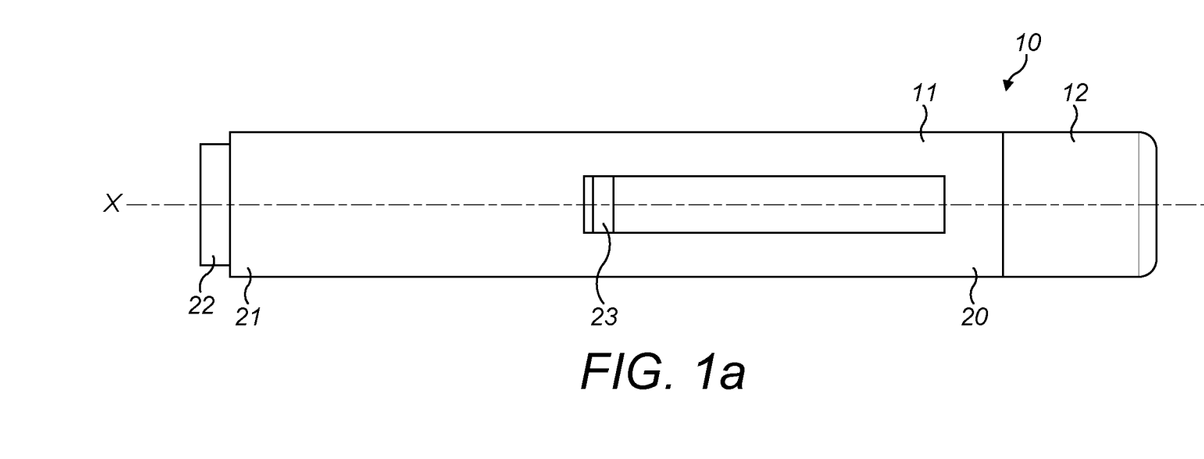
FIG. 1A is a schematic side view of an injection device according to the disclosure, with a cap attached to a body of the injection device.
Figure 1B:
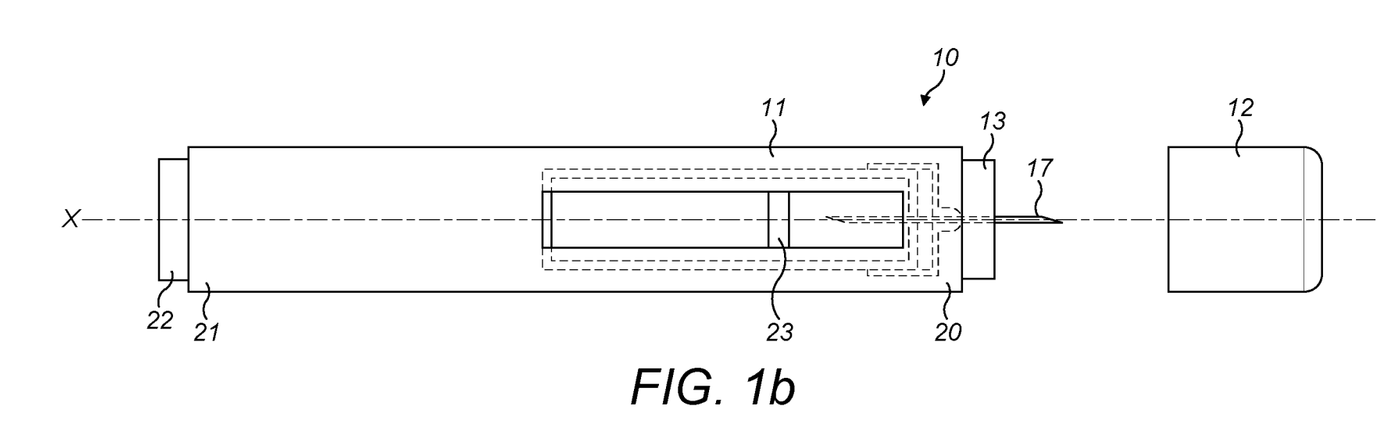
FIG. 1B is a schematic side view of the injection device of FIG. 1A, with the cap removed from the body.

According to some embodiments of the present disclosure, an exemplary drug delivery device 10 is shown in FIGS. 1A & 1B. Device 10, as described above, is configured to inject a medicament into a patient's body. Device 10 includes a housing 11 (e.g., an injector body) which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
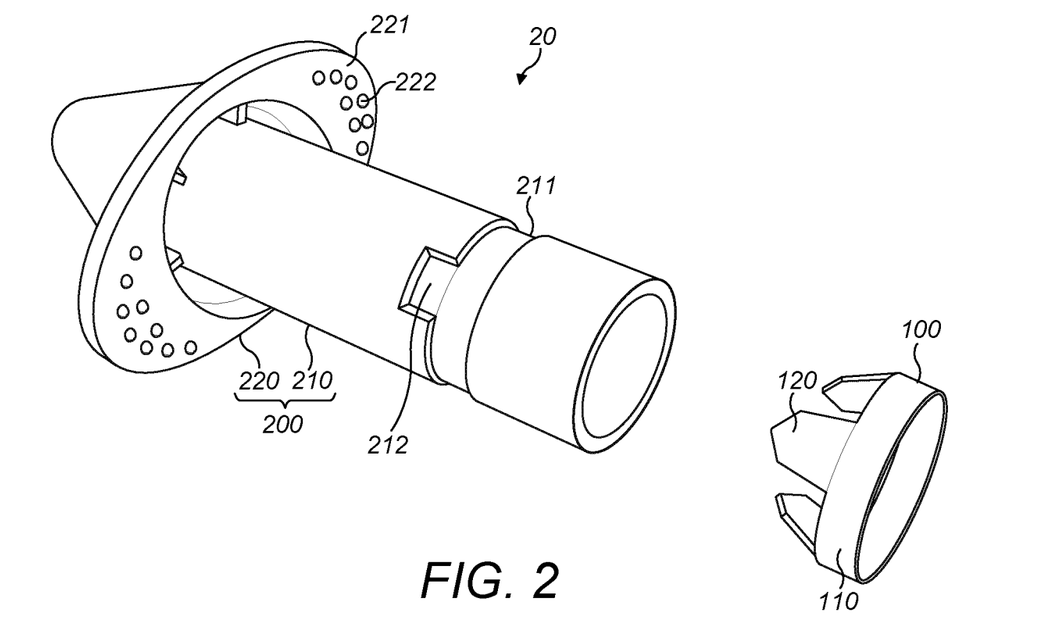
FIG. 2 is an isometric view of a cap for the FIGS. 1A and 1B injection device according to a first embodiment of the disclosure.

With reference to FIG. 2, a cap 20 for use with an injector body of an injection device (e.g., such as for use with the housing 11 of the injection device 10, shown in FIGS. 1A & 1B) according to a first embodiment is 20 shown. The cap 20 comprises a barbed engaging member 100 which is formed separately from a main body 200 of the cap 20. FIG. 2 shows the cap 20 in a disassembled state.

The engaging member 100 is formed as a cylindrical ring 110, having a plurality of barbs 120 which extend from the ring 110. The barbs 120 are disposed at an angle, extending radially inwards towards a central axis of the cylindrical ring 110 and also extending axially away from the plane of the ring 110. Where the engaging member 100 is aligned with the longitudinal axis of the injection device, the barbs 120 extend distally and radially inwards from a distal end face of the cylindrical ring 110.

The outer diameter of the ring 110 is smaller than an opening at the distal end of the injection device, such that the engaging member 100 is able to pass through the opening into an interior of the injection device. The distance between the barbs 120 at their closest point defines an inner diameter of the engaging member 100, that is, the diameter of the largest circle which is centred on the longitudinal axis of the ring 110 and positioned between the barbs 120 at their closest point. The inner diameter of the engaging member 100 is smaller than the outer diameter of the rubber needle for a syringe which is used in the injection device.

The engaging member 100 is machined from metal or, alternatively, may be formed from a hard plastic by, for example, a molding process or a 3D printing process. Each of the barbs 120 comprises an engaging edge disposed at the radially inward end of the barb. The barbs 120 are formed to extend and terminate at a triangular point, and so each engaging edge is an arrow-shaped edge formed on the inner surface of the respective barb.

The main body 200 of the cap 20 comprises a first part 210 and a second part 220. The first part 210 is a hollow cylinder which is open at the proximal end. The distal end of the first part 210 is attached to the second part 220, with the hollow cylinder of the first part 210 being closed at the distal end by the second part 220. The outer diameter of the cylinder is the same as the outer diameter of the engaging member 100. The first part 210 of the main body 200 is able to pass through the opening in the distal end of the injection device into the interior of the injection device.

A groove portion 211 of the first part 210 has an outer diameter which is smaller than the outer diameter of the rest of the cylinder. The groove portion 211 is positioned along the length of the cylinder, towards the proximal end of the first part 210. The outer diameter of the groove portion 211 is the same as the inner diameter of the engaging member 100. The longitudinal extent of the groove portion 211 is the same as the longitudinal extent of the ring 110 of the engaging member 100. The ring 110 of the engaging member 100 is received in the groove portion 211, and the outer surface of the ring 110 lies flush with the outer surface of the first part 210 of the main body 200.

The first part 210 further comprises a plurality of openings 212, where the number of openings 212 corresponds to the number of barbs 120 on the engaging member 100. The openings 212 are disposed adjacent to the distal end of the groove portion 211. The openings 212 are spaced around the circumference of first part 210, so as to align with the barbs 120 of the engaging member 100. The openings 212 are arranged to receive the barbs 120 of the engaging member 100 such that, when the ring 110 of the engaging member 100 is received by the groove portion 211, the barbs 120 pass through the openings 212 of the first part 210 into the interior of the cap 20.

Figure 3:
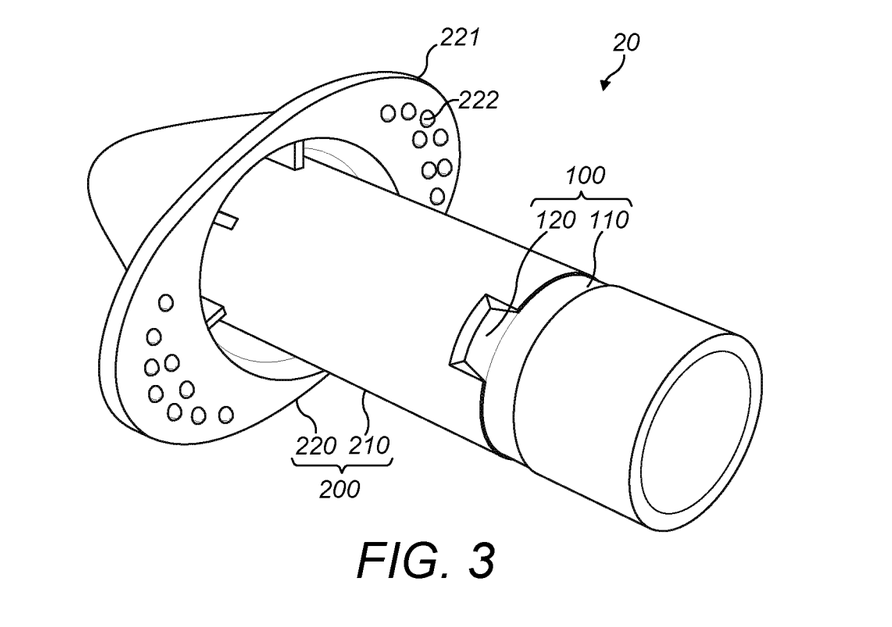
FIG. 3 is an isometric view of the cap of FIG. 2.

FIG. 3 shows the cap 20 of the first embodiment in an assembled state. The first part 210 of the main body 200 is formed from an elastic material such as rubber, which may be natural rubber, synthetic rubber or a mixture thereof. During assembly the hollow cylinder of the first part 210 is compressed at the proximal end and can be passed through the ring 110 of the engaging member 100. The engaging member 100 is moved along the length of the main body 200 until the ring 110 of the engaging member 100 is received in the groove portion 211 of the first part 210 of the main body 200. The proximal end of the main body 200 is released and returns to its original shape. The proximal end of the hollow cylinder retains the engaging member 100 in the grooved portion of the first part 210 of the main body 200. The plurality of barbs 120 pass through the corresponding openings 212 and the outer surface of the engaging member 100 lies flush with the outer surface of the main body 200.

The second part 220 of the main body 200 is formed in the shape of a bell or a rounded cone with an opening at the proximal end and a peak at the distal end. The second part 220 further comprises a rim 221 extending radially outwards from the opening. The inner diameter of the opening is larger than the outer diameter of the first part 210, such that the first part 210 is received within the opening of the second part 220. The hollow cylinder of the first part 210 is closed at a distal end by the peak of the second part 220.

The inner diameter of the opening is larger than the distal end of the injection body, and the distal end of the injection body can be received within the opening of the second part 220. The rim 221 is formed around the outer circumference of the opening and extends radially outwards. The rim 221 is elliptical and forms two handles at opposite sides of the cap 20, where the long axis of the rim 221 extends further outwards. The handles are textured with, for example, small protrusions 222 or indentations, to allow the handles to be gripped more easily.

The second part 220 of the main body 200 is made from rubber and is formed as a single piece with the first part 210 of the main body 200. Alternatively, the second part 220 may be formed from a hard plastic and bonded to the first part 210.

The cap 20 is pushed onto the distal end of the injection device when preparing the device. A syringe is placed within the injection device and then the cap 20 is pushed onto the distal end of the injection device. The syringe comprises a medicament reservoir, a needle, and a rubber needle shield covering the needle. The needle, covered by the rubber needle shield, is at the distal end of the syringe when placed within the injection device and is located within the opening at the distal end of the injection device.

When the cap 20 is pushed onto the distal end of the injection device, the first part 210 of the main body 200 and the engaging member 100 are received in the opening at the distal end of the injection device. The hollow cylinder of the first part 210 and the engaging portion pass over the rubber needle shield, which is disposed within the opening of the injection device. The second part 220 of the cap 20 fits over the distal end of the injection device and closes the opening in the distal end of the device. The cap 20 therefore seals the injection device and protects the needle before the injection device is used.

The barbs 120 of the engaging member 100 extend into the interior of the cap 20 and contact the rubber needle shield when the cap 20 is pushed onto the injection device. The inner diameter of the engaging member 100 is smaller than the outer diameter of the rubber needle shield. However, the barbs 120 of the engaging member 100 are angled towards the distal end of the cap 20 and the rubber needle shield can be compressed by the barbs 120 to pass through the engaging member 100 in a distal direction.

The engaging member 100 is positioned such that the rubber needle shield is passed partially through the engaging member 100 when the cap 20 is pushed onto the injection device. The barbs 120 of the engaging member 100 remain in contact with the rubber needle shield while the cap 20 remains on the injection device.

The cap 20 is removed from the injection device before it can be used. The second part 220 of the cap 20 can be gripped by the user to pull the cap 20 from the injection device, or the user may push against the rim 221 of the second part 220 to remove the cap 20.

The barbs 120 of the engaging member 100 are in contact with the rubber needle shield and are angled towards the distal end of the injection device. When the cap 20 is moved out of the distal end of the injection device, the engaging edge of each barb 120 engages with the outer surface of the rubber needle shield. The rubber needle shield is retained by the barbs 120 of the engaging member 100, which exert a force to push the rubber needle shield in the distal direction.

As the cap 20 is removed from the injection device, the rubber needle shield is retained within the cap 20 and is removed from the needle. The needle of the syringe is therefore exposed when the cap 20 is removed and the injection device is ready for use.

The cap 20 for an injection device according to the first embodiment improves the usability of the injection device by providing means for simultaneously removing the cap 20 and the rubber needle shield. Furthermore, the external appearance of the cap 20 is similar to that of a conventional cap 20 and does not require an additional opening at the distal end to remove the rubber needle shield. As such, in appearance and in use the cap 20 appears normal to the user and therefore provides the improved operation of the injection device without additional complexity for the user.

Figure 4:
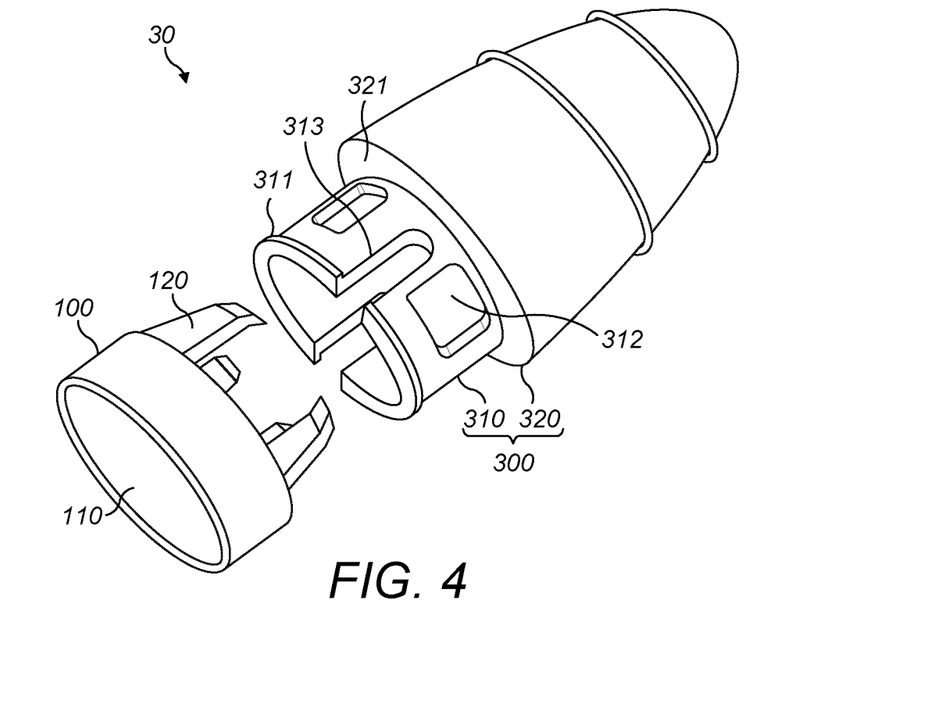
FIG. 4 is an isometric view of a cap for the FIGS. 1A and 1B injection device according to a second embodiment of the disclosure.

With respect to FIG. 4, a cap 30 for use with an injector body of an injection device (e.g., such as for use with the housing 11 of the injection device 10, shown in FIGS. 1A & 1B) according to a second embodiment is described. Elements other than those described are substantially as described with respect to the first embodiments.

A main body 300 of the cap 30 comprises a first part 310 and a second part 320. The first part 310 is a hollow cylinder which is open at the proximal end. The distal end of the first part 310 is attached to the second part 320, with the hollow cylinder of the first part 310 being closed at the distal end by the second part 320. The outer diameter of the cylinder is the same as the inner diameter of the engaging member 100. The longitudinal extent of the cylinder is the same as the longitudinal extent of the ring 110 of the engaging member 100. At the proximal end of the cylinder, the first part 310 further comprises a retaining element 311 which has a larger diameter than the outer diameter of the cylinder. The ring 110 of the engaging member 100 is received over the cylinder of the first part 310 and is held in position by the retaining element 311.

The first part 310 of the main body 300 is formed from plastic or, alternatively, from rubber. The hollow cylinder comprises two slots 313 which extend axially from the proximal end of the cylinder. The slots 313 are positioned at opposite points on the circumference of the first part 310, such that the proximal end of the first part 310 is divided into two equal portions.

The second part 320 of the main body 300 is formed in the shape of a rounded cone, with an opening at the proximal end and a peak at the distal end. The proximal end of the second part 320 has a larger diameter than the outer diameter of the first part 310, and so the second part 320 extends radially outwards from the distal end of the first part 310 and then tapers to the peak at the distal end of the second part 320. The outer diameter of the second part 320 at its widest point is the same as the inner diameter of the injection device. The second part 320 of the main body 300 is made from plastic and is formed as a single piece with the first part 310 of the main body 300. Alternatively, the first part 310 and the second part 320 of the main body 300 may be formed from a single piece of rubber.

The proximal end of the second part 320 extends outwards from the first part 310 of the main body 300 and forms a proximally facing end surface 321. The main body 300 of the cap 30 further comprises a plurality of openings 312, where the number of openings 312 corresponds to the number of barbs 120 on the engaging member 100. Each of the openings 312 extends from the first part to the second part of the main body 300. The openings 312 extend axially along a part of the length of the hollow cylinder at the distal end of the first part 310 and outwards across a part of the radial extent of the proximal end surface 321 of the second part 320. The openings 312 are spaced around the circumference of the main body 300, so as to align with the barbs 120 of the engaging member 100. The openings 312 are arranged to receive the barbs 120 of the engaging member 100 such that, when the ring 110 of the engaging member 100 is received over the first part 310, the barbs 120 pass through the opening of the main body 300 into the interior of the cap 30.

Figure 5:
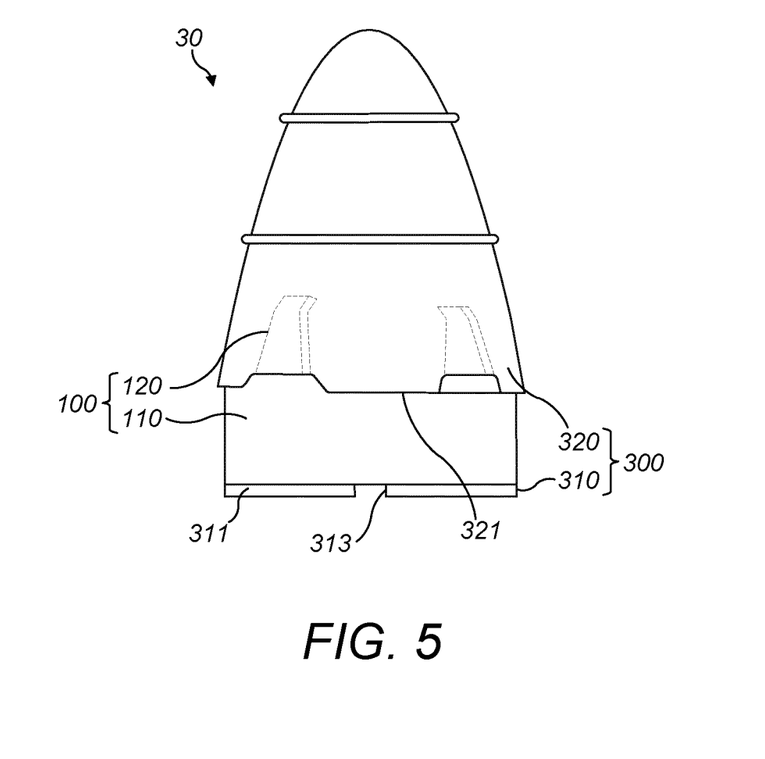
FIG. 5 is a schematic cross-sectional side view of the cap of FIG. 4.

FIG. 5 shows the cap 30 of the second embodiment in an assembled state. During assembly the two portions of the first part 310 are pressed together at the proximal end and can be passed through the ring 110 of the engaging member 100. The engaging member 100 is moved along the length of the main body 300 until the plurality of barbs 120 pass through the corresponding openings 312 into the interior of the cap 30 and a distal end surface of the ring 110 of the engaging member 100 abuts with the proximally facing end 321 surface of the second part. The proximal end of the main body 300 is released and returns to its original shape, such that the engaging member 100 is held in position by the retaining element 311 at the proximal end and the end surface 321 of the second part 320 at the distal end.

When the cap 30 is pushed onto the distal end of the injection device, the first part 310 of the main body 300 and the engaging member 100 are received in the opening at the distal end of the injection device. The hollow cylinder of the first part 310 and the engaging member 100 pass over the rubber needle shield, which is disposed within the opening of the injection device. The second part 320 of the cap 30 is received within the distal end of the injection device and plugs the opening in the distal end of the device. The cap 30 therefore seals the injection device and protects the needle before the injection device is used.

The barbs 120 of the engaging member 100 extend into the interior of the cap 30 and contact the rubber needle shield when the cap 30 is pushed onto the injection device. The inner diameter of the engaging member 100 is smaller than the outer diameter of the rubber needle shield. However, the barbs 120 of the engaging member 100 are angled towards the distal end of the cap 30 and the rubber needle shield can be compressed by the barbs 120 to pass through the engaging member 100 in a distal direction.

The engaging member 100 is positioned such that the rubber needle shield is passed partially through the engaging member 100 when the cap 30 is pushed onto the injection device. The barbs 120 of the engaging member 100 remain in contact with the rubber needle shield while the cap 30 remains on the injection device.

To remove the cap 30 from the injection device before use, the second part 320 of the cap 30 can be gripped by the user to pull the cap 30 from the injection device. The barbs 120 of the engaging member 100 are in contact with the rubber needle shield and are angled towards the distal end of the injection device. When the cap 30 is moved out of the distal end of the injection device, the engaging edge of each barb 120 engages with the outer surface of the rubber needle shield. The rubber needle shield is retained by the barbs 120 of the engaging member 100, which exert a force to push the rubber needle shield in the distal direction.

As the cap 30 is removed from the injection device, the rubber needle shield is retained within the cap 30 and is removed from the needle. The needle of the syringe is therefore exposed when the cap 30 is removed and the injection device is ready for use.

The cap 30 for an injection device according to the second embodiment improves the usability of the injection device by providing means for simultaneously removing the cap 30 and the rubber needle shield. Furthermore, the external appearance of the cap 30 is similar to that of a conventional cap 30 and does not require an additional opening at the distal end to remove the rubber needle shield. As such, in appearance and in use the cap 30 appears normal to the user and therefore provides the improved operation of the injection device without additional complexity for the user.

Figure 6:
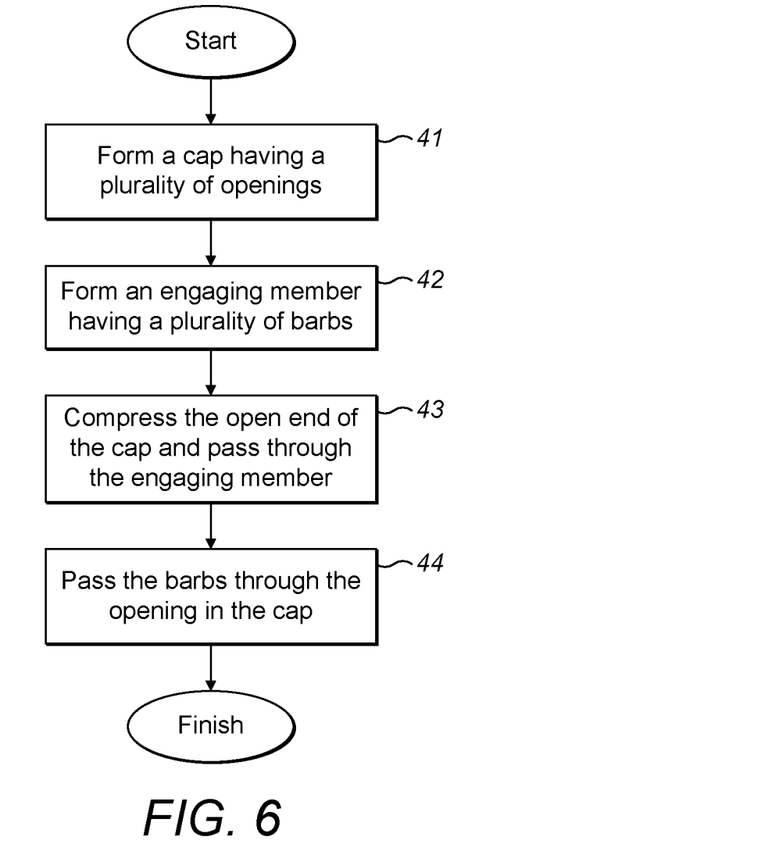
FIG. 6 is a flow chart showing a method of manufacturing.

With respect to FIG. 6, a method of manufacture is shown, to manufacture a cap for the injection device of the first or second embodiment. The method comprises forming, at step 41, a main body which has a first open end and a second closed end, and one or more openings through an outer surface of the main body. Next, at step 42, forming an engaging member which comprises a ring and one or more protruding elements arranged to extend inwards from the ring. Once the parts are formed, the method includes compressing, at step 43, the open end of the main body and passing the open end of the main body through the ring of the engaging member and passing, at step 44, the one or more protruding elements through the one or more openings of the main body.

Although a few embodiments of the present disclosure have been shown and described, it will be appreciated by those skilled in the art that changes may be made in these embodiments without departing from the disclosure, the scope of which is defined in the appended claims. Various components of different embodiments may be combined where the principles underlying the embodiments are compatible.

For example, the engaging element of either embodiment may include any number of barbs arranged in one or more rings or, alternatively, may comprise only a single barb. The barbs of the engaging element may also be formed as a plurality of hooks which are directed inwards from the ring of the engaging element. A plurality of protruding elements of different forms may be used to ensure the needle shield is gripped tightly.

The main body may be formed as a single piece or in multiple parts made from any suitable material. The main body of the second embodiment may include any number of slots for compressing the proximal end of the first part, or the proximal end of the first part may be compressed with only a single slot.

The cap of either embodiment may be used as part of an auto-injector device which includes any of an automatic needle insertion mechanism, an automatic medicament dispensing mechanism or an automatic cap removal mechanism. Alternatively, the cap may be part of a manual injection device in which a needle syringe is mounted to assist the user with a medicament delivery. Alternatively, the cap may be used as a needle shield removal device to easily remove the rubber needle shield from a syringe.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta-¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An injection device comprising:
    an injector body arranged for mounting a syringe with a needle shield; and
    a cap disposed at one end of the injector body, wherein the cap comprises:
        a main body with a first open end and a second closed end, the main body comprising a groove portion, a retaining element that defines the first open end, and one or more openings through an outer surface, wherein the groove portion has an outer diameter that is smaller than an outer diameter of the retaining element, and wherein the one or more openings are disposed adjacent to a distal end of the groove portion,
        an engaging member disposed externally on the main body and received in the groove portion such that an outer surface of the engaging member lies flush with an outer surface of the retaining element, wherein the engaging member comprises one or more protruding elements arranged to extend inwards respectively through the one or more openings in the outer surface of the main body and configured to engage with the needle shield,
    wherein the engaging member comprises a ring that is arranged externally around the main body, and wherein the one or more protruding elements are arranged to extend inwards from the ring at an angle to a plane of the ring.

2. The injection device of claim 1, wherein the one or more protruding elements are formed as a plurality of barbs which are arranged to engage with the needle shield when the cap is pulled away from the injector body.

3. The injection device of claim 1, wherein the one or more protruding elements are formed as a plurality of hooks which are arranged to engage with the needle shield when the cap is pulled away from the injector body.

4. The injection device of claim 1, wherein the first open end of the main body is configured to be compressed, and wherein the first open end of the main body is arranged to pass through the ring of the engaging member when the first open end of the main body is compressed.

5. The injection device of claim 4, wherein the main body comprises one or more slots extending from the first open end, the one or more slots being configured to allow compression of the first open end of the main body.

6. The injection device of claim 1, wherein the main body comprises a rubber material.

7. The injection device of claim 1, wherein the engaging member is disposed entirely within the groove of the main body.

8. A cap for use with an injection device, wherein the cap comprises:
   a main body with a first open end and a second closed end, the main body comprising a groove portion, a retaining element that defines the first open end, and one or more openings through an outer surface, wherein the groove portion has an outer diameter that is smaller than an outer diameter of the retaining element, and wherein the one or more openings are disposed adjacent to a distal end of the groove portion; and
   an engaging member disposed externally on the main body and received in the groove portion such that an outer surface of the engaging member lies flush with an outer surface of the retaining element, wherein the engaging member comprises one or more protruding elements arranged to extend inwards respectively through the one or more openings in the outer surface of the main body and configured to engage with a needle shield of the injection device,
   wherein the engaging member comprises a ring that is arranged externally around the main body, and wherein the one or more protruding elements are arranged to extend inwards from the ring at an angle to a plane of the ring.

9. The cap of claim 8, wherein the one or more protruding elements are formed as a plurality of barbs or a plurality of hooks.

10. The cap of claim 8, wherein the first open end of the main body is configured to be compressed, and wherein the first open end of the main body is arranged to pass through the ring of the engaging member when the first open end of the main body is compressed.

11. The cap of claim 10, wherein the main body comprises one or more slots extending from the first open end, the one or more slots being configured to allow compression of the first open end of the main body.

12. A method of manufacturing a cap of an injection device, wherein the injection device further comprises an injector body configured for mounting a syringe with a needle shield, wherein the cap is configured to be disposed at one end of the injector body, and wherein the method comprises:
   forming a main body of the cap with a first open end and a second closed end, the main body comprising a groove portion, a retaining element that defines the first open end, and one or more openings through an outer surface, wherein the groove portion has an outer diameter that is smaller than an outer diameter of the retaining element, and wherein the one or more openings are disposed adjacent to a distal end of the groove portion;
   forming an engaging member of the cap, the engaging member disposed externally on the main body and received in the groove portion such that an outer surface of the engaging member lies flush with an outer surface of the retaining element, wherein the engaging member comprises one or more protruding elements arranged to extend inwards respectively through the one or more openings in the outer surface of the main body and configured to engage with the needle shield of the injection device;
   compressing the first open end of the main body and passing the first open end of the main body between the one or more protruding elements of the engaging member; and
   passing the one or more protruding elements through the one or more openings of the main body,
   wherein the engaging member comprises a ring that is arranged externally around the main body, and wherein the one or more protruding elements are arranged to extend inwards from the ring at an angle to a plane of the ring.

* * * * *